United States Patent
Hiselius

[19]

[11] Patent Number: 5,815,842
[45] Date of Patent: Oct. 6, 1998

[54] EAR PROTECTION CAP WITH IMPROVED SOUND ABSORPTION

[75] Inventor: Per Hiselius, Lund, Sweden

[73] Assignee: Dalloz Safety AB, Billesholm, Sweden

[21] Appl. No.: 909,658

[22] Filed: Aug. 12, 1997

Related U.S. Application Data

[63] Continuation of Ser. No. 495,470, filed as PCT/SE94/00082, Feb. 2, 1994, published as WO94/17763, Aug. 18, 1994, abandoned.

[30] Foreign Application Priority Data

Feb. 10, 1993 [SE] Sweden ................................ 9300437-2

[51] Int. Cl.⁶ ............................ A01F 11/02; G10K 11/04
[52] U.S. Cl. ................. 2/209; 128/867; 181/129
[58] Field of Search ............................ 2/208, 209, 423; 181/129, 136, 198, 284, 288; 128/864, 867, 866

[56] References Cited

U.S. PATENT DOCUMENTS

| | | |
|---|---|---|
| 3,117,575 | 1/1964 | Carrell et al. ........................ 181/129 |
| 3,432,861 | 3/1969 | Flagg ........................................ 2/209 |
| 3,506,980 | 4/1970 | Aileo ........................................ 2/209 |
| 3,593,819 | 7/1971 | Giraudeau .............................. 181/288 |
| 3,875,592 | 4/1975 | Aileo ........................................ 2/209 |
| 4,113,053 | 9/1978 | Matsumoto et al. ................... 181/288 |
| 4,120,382 | 10/1978 | Bschorr .................................. 181/198 |

FOREIGN PATENT DOCUMENTS

| | | |
|---|---|---|
| 2517703 | 11/1976 | Germany . |
| 3623315 | 1/1988 | Germany . |
| 3825875 | 2/1990 | Germany .............................. 181/129 |
| WO 90/15584 | 12/1990 | WIPO . |

Primary Examiner—Michael A. Neas
Attorney, Agent, or Firm—Burns, Doane, Swecker & Mathis, L.L.P.

[57] ABSTRACT

An earmuff incorporating elevated sound attenuation. The earmuff comprises an outer cup (10') which connects with a sealing part. Arranged within the earmuff are a plurality of separating partitioning walls (14) which extend from the bottom wall (16) of the cup towards the sealing part. The partitioning walls (14) may be integral with the cup (10') or formed separately therefrom and loosely fitted thereinto.

12 Claims, 3 Drawing Sheets

EAR PROTECTION CAP WITH IMPROVED SOUND ABSORPTION

This application is a continuation of application Ser. No. 08/495,470, filed Jul. 26, 1995, filed as PCT/SE94/00082 Feb. 2, 1994 published as WO94/17763 Aug. 18, 1994, now abandoned.

BACKGROUND AND SUMMARY

The present invention relates to an earmuff which incorporates elevated acoustic attenuation and which comprises an outer shell or cup made of a rigid plastic material, preferably polypropylene, and a softer sealing part which connects with the outer cup and is intended to lie around one ear of the wearer, wherein the muff interior may also include sound attenuating inserts, for instance inserts made of plastic foam or like material.

As is known, an earmuff, or ear protector, is intended to form an acoustic barrier between an ear of the wearer and a source of sound. Attenuation is effected by virtue of the earmuff preventing sound waves from reaching the ear. If the cup is not sufficiently rigid, it is unable to retain its shape when subjected to high noise levels and will begin to oscillate under the influence of the driving acoustic force, this oscillation being referred to here as "co-oscillation". This co-oscillation propagates the sound and impairs the acoustic attenuating effect of the earmuff. In order to prevent such impairment, it is important that both of the cups included in a hearing protector or earmuff are sufficiently rigid, this requirement being satisfied by appropriate selection of material, material thickness and shape. A sound attenuating cup which has a rounded or bulging surface is more rigid than a cup that has a flat surface. For this reason, the majority of present-day earmuffs are dished. It is normally necessary to provide reinforcements in those instances in which flat surfaces are used.

U.S. Pat. No. 3,432,861 teaches an earmuff which has a rounded surface and the cup of which is provided internally with ridges which extend in mutually different directions. The ridges, or like elevations, have a relatively small height in relation to the height of the earmuff and are intended to provide the cup with the mechanical strength required to improve the sound attenuating effect of the earmuff.

U.S. Pat. No. 3,875,592 also teaches an earmuff which has a rounded surface and with which the cup, as seen from its outside, is provided with recesses or grooves which extend into the interior of the cup and therewith form corresponding outwardly projecting ridges or fins. The cup is reinforced by the fins produced by this arrangement and the fins have a relatively small height in relation to the total height of the cup.

The object of the invention is primarily to further improve the acoustic attenuation of an earmuff or hearing protector of the aforesaid kind. In this regard, it is not the intention of the invention to reinforce the actual cup itself, but to provide improved attenuation of sound waves within the earmuff, so as to enable resonances within the earmuff to be eliminated, among other things. This object is achieved by constructing an earmuff of the kind defined in the introduction.

According to the present invention, it is important that the partitioning walls provided in the earmuff spaces which have a substantial height in relation to the major part of the height of the earmuff, so that sound waves will not "slip" beyond the extension of the partitioning walls. The partitioning walls will thus preferably extend as close as possible to the place where the ear of a wearer is intended to lie. The partitioning walls will preferably extend over the greater part of the height of the earmuff. An advantage is afforded when the partitioning walls are orientated so that sound waves are greatly dampened during their passage in the earmuff, as a result of a large number of reflections between said walls.

The cup partitioning walls may either be formed integrally with the actual cup itself or may be formed separately. In this latter case, the partitioning walls will preferably form a continuous grid unit which can be placed loosely in the cup so as to rest against the inner surfaces thereof. This latter method simplifies manufacture of the cup.

BRIEF DESCRIPTION OF THE DRAWINGS

The features and advantages of the present invention are well understood by reading the following detailed description in conjunction with the drawing in which like numerals indicate similar elements and in which.

DETAILED DESCRIPTION

Figure 1:
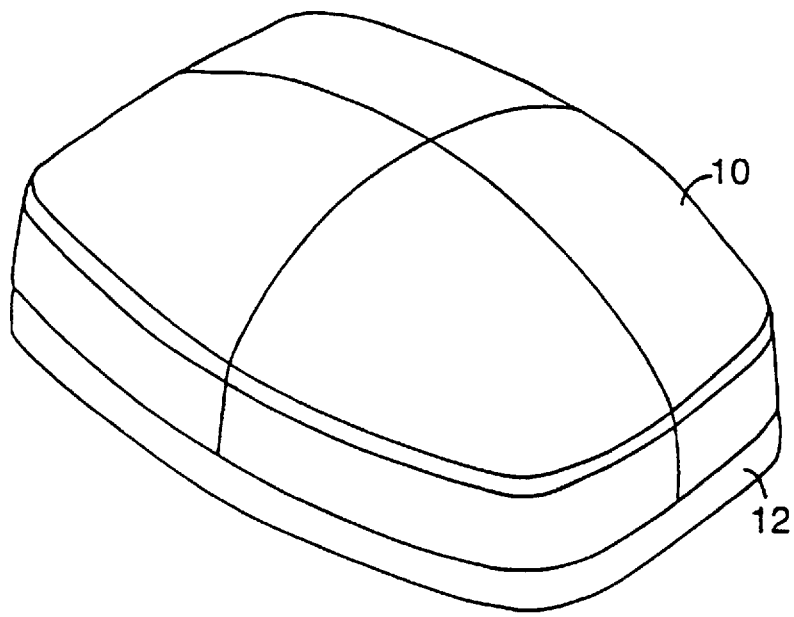
FIG. 1 illustrates in perspective an embodiment of a conventional earmuff and shows the earmuff from its outside.

An earmuff which includes any one of the arrangements illustrated in FIGS. 1–6 is intended to be included in a complete hearing protector (not shown in the drawings) which comprises two earmuffs which are intended to be fitted tightly around respective ears of the wearer. The two earmuffs can be mutually joined by means of a strap or headband in a known manner. The earmuffs may also be provided with means which enable them to be connected to a protective helmet or some like device.

The earmuff illustrated in FIG. 1 includes an outer attenuation cup or shell 10, which is normally comprised of a rigid plastic material, preferably polypropylene. Adjacent that part of the cup 10 which is intended to lie around the ear of the wearer is a separate sealing part 12. This sealing part has the form of a soft foamed plastic ring which is normally covered externally with plastic foil. It is important that the sealing part 12 lies as tightly as possible around the ear of the wearer while, at the same time, feeling comfortable, i.e. the ring shall have overall soft abutment with the ear.

In the case of the FIG. 1 embodiment, the cup 10 has a slightly rounded configuration. This configuration guarantees a stable construction, since it will not begin to vibrate, i.e. co-oscillate, at those acoustic frequencies to which it is normally subjected.

Figure 2:
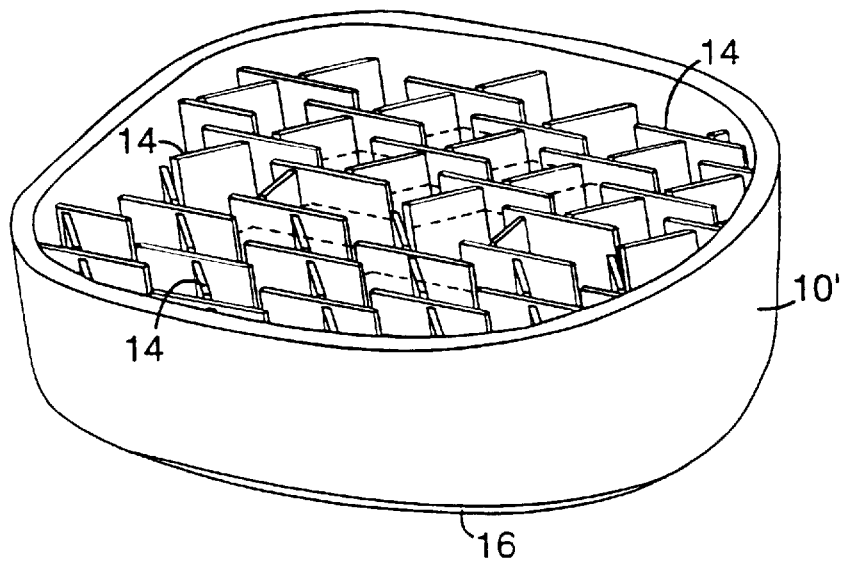
FIG. 2 is a perspective view of the parts provided within the cup of an earmuff and essential to the present invention.

According to FIG. 2, the cup 10' of one earmuff is provided with a plurality of cup-space partitioning walls 14, which have mutually different lengths and mutually different positions. The sealing part 12 shown in FIG. 1 has been omitted in the FIG. 2 illustration. Although not shown, the earmuff will also include a sound attenuating insert, preferably a foamed plastic insert, which is located adjacent the opening of the earmuff that faces towards the ear of the wearer. This insert has also been omitted from the FIG. 2 illustration, in order to better illustrate the inventive partition wall arrangement.

The partitioning walls extend from the bottom 16 of the cup 10', this bottom being generally flat in the illustrated case, and upwards towards the place intended for the ear. It will be seen from the Figure that the walls 14 have a substantial height, which will preferably be more than half of the total height of the earmuff. The partitioning walls 14 are orientated in a manner to eliminate or dampen resonances that occur within the earmuff. The partitioning walls are preferably made of polypropylene and are angled to one another so as to provide good attenuation with repeated reflection of the sound waves. In the illustrated case, the intermediate walls 14 are formed integrally with the cup 10' and are thus manufactured simultaneously therewith in one single moulding operation. It may sometimes be convenient, however, for manufacturing reasons of a technical nature to produce the actual cup 10' and the partitioning walls 14 separately from one another. In this latter case, the partitioning walls 14 will preferably hang together, which can be achieved by virtue of a mutual joining bottom surface in the form of a thin plastic layer. The partitioning walls can then be placed loosely in the cup in the form of a unit, and the unit can be secured in the cup by pressing or gluing the unit onto the bottom of the cup.

Figure 3:
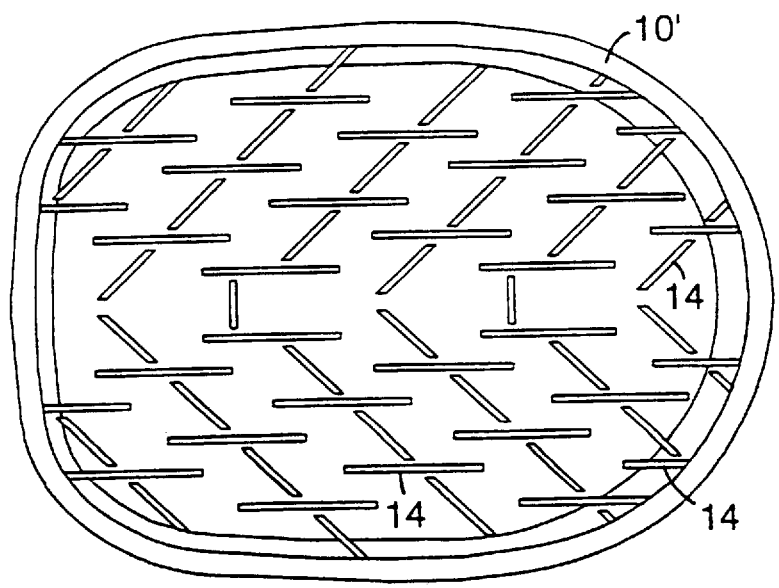
FIG. 3 illustrates the arrangement shown in FIG. 2 from above.

FIG. 3 illustrates the arrangement shown in FIG. 2 directly from above, and illustrates the configuration and mutual positioning of the partitioning walls 14 more clearly than FIG. 2. The partitioning walls 14 form a symmetrical pattern in this case, although such pattern symmetry is not absolutely necessary.

Figure 4:
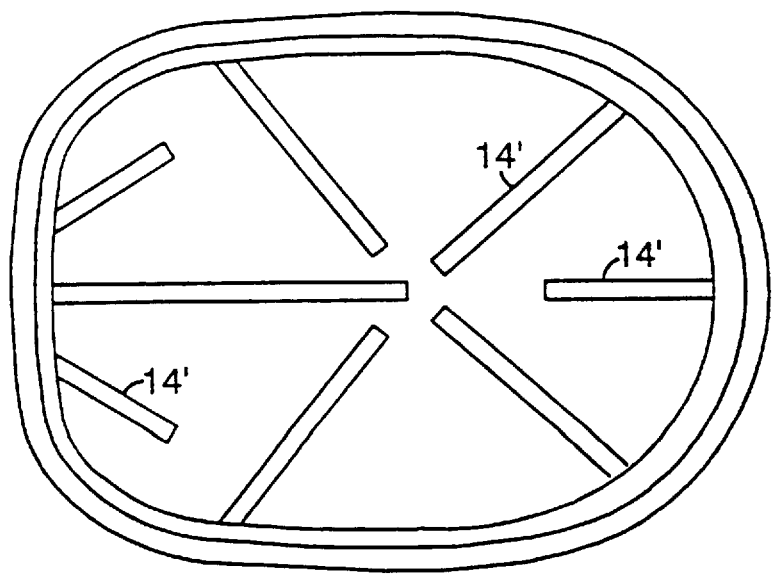
FIGS. 4, 5, 6 and 7 are examples of different embodiments of a partition wall arrangement configured in accordance with the invention and capable of being included in the cup of an earmuff.
Figure 5:
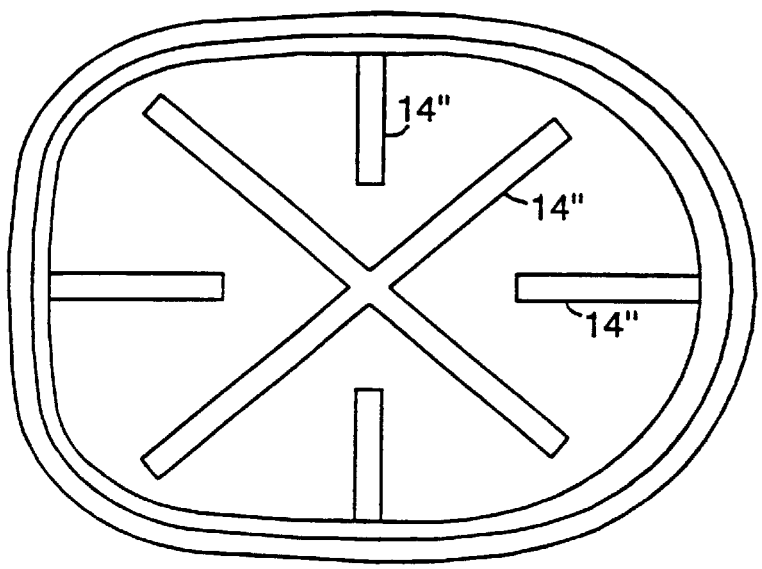
Figure 6:
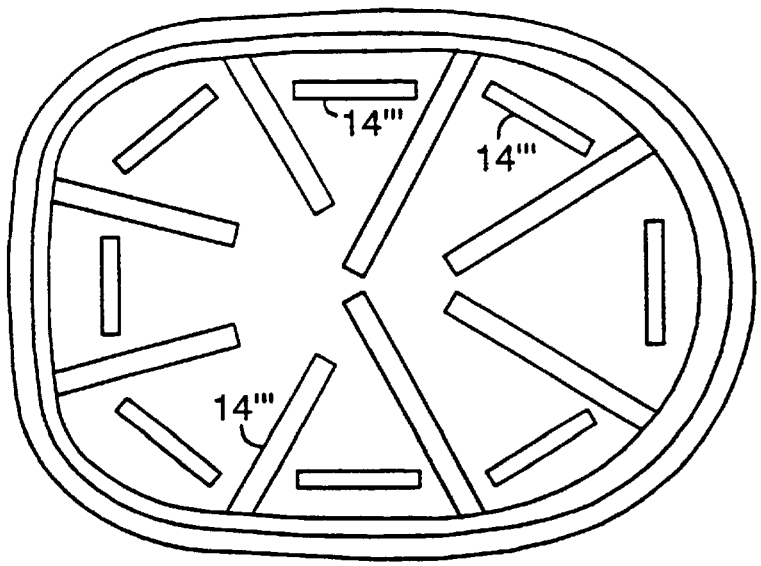
Figure 7:
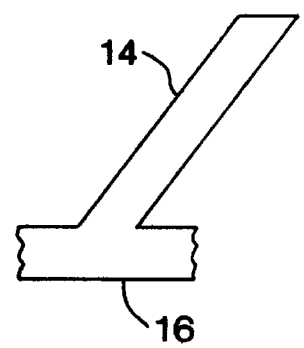

FIGS. 4, 5 and 6 show further examples of other advantageous positions of the partitioning walls 14', 14" and 14'" respectively. All embodiments are intended to provide the best possible sound attenuation. It is also conceivable to arrange the partitioning walls in a manner to form small sound-proof cells. With suitable dimensioning, standing waves are then able to occur in the cells, although only at frequencies which lie outside the audible frequency range. The walls may conveniently be inclined to the bottom of the cup, so as to reduce the number of reflections that are directed towards the ear.

Naturally, the mutual positioning of the partitioning walls and their positioning in relation to the cup will prefer, ably always be in relation to those frequencies of the sound waves that are to be attenuated.

The frequency of a standing wave is inversely proportional to the distance between the walls between which the wave occurs. The partitioning walls are primarily intended to improve attenuation at frequencies above 1,500 Hz and the distance between the walls in the earmuff will preferably not exceed 2 cm.

I claim:

1. An earmuff comprising:

an outer cup made of a rigid plastic material, the outer cup having an interior space;

a sealing part connected to the cup, the sealing part, in use, being disposed around an ear of the wearer, the sealing part being softer than the outer cup; and a plurality of separating partitioning walls disposed in the interior space such that the separating partitioning walls project from a bottom wall of the earmuff in a direction towards the sealing part, the separating partitioning walls preventing occurrence of standing waves within an audible frequency range;

wherein the partitioning walls extend over more than half of a height of the cup over an entire length of the partitioning walls, and the walls are oriented such that they attenuate sound waves during passage of the sound waves in the earmuff by reflection between the walls.

2. An earmuff according to claim 1, wherein the partitioning walls are arranged such that sound waves are attenuated by reflection between a plurality of different reflection points of two or more walls.

3. An earmuff according to claim 1, wherein the partitioning walls delimit a plurality of cells.

4. An earmuff according to claim 1, wherein the partitioning walls are integral with the cup.

5. An earmuff according to claim 1, wherein a distance between two mutually opposing partitioning walls is less than 2.0 cm.

6. An earmuff according to claim 1, wherein the partitioning walls are inclined in relation to a bottom of the cup.

7. An earmuff according to claim 1, wherein ones of the partitioning walls at a central part of the cup terminate at a greater distance from a plane through an opening in the cup than at a periphery of the cup.

8. An earmuff according to claim 2, wherein the partitioning walls are integral with the cup.

9. An earmuff according to claim 3, wherein the partitioning walls are integral with the cup.

10. An earmuff according to claim 2, wherein the partitioning walls are inclined in relation to a bottom of the cup.

11. An earmuff according to claim 2, wherein ones of the partitioning walls at a central part of the cup terminate at a greater distance from a plane through an opening in the cup than at a periphery of the cup.

12. An earmuff according to claim 2, wherein an increase in attenuation obtained by the partitioning walls occurs from and with about 1,500 p/s.

\* \* \* \* \*